United States Patent [19]

Sawamura et al.

[11] Patent Number: 4,873,194

[45] Date of Patent: Oct. 10, 1989

[54] PROCESS FOR PREPARING ENZYME PREPARATION

[75] Inventors: Norio Sawamura, Hashimoto; Takaharu Matsuo, Sennan; Kazunobu Tsumura, Sakai; Yoshitaka Ebihara, Yao, all of Japan

[73] Assignee: Fuji Oil Company, Limited, Osaka, Japan

[21] Appl. No.: 56,409

[22] Filed: May 29, 1987

[51] Int. Cl.$^4$ ............................................. C12N 9/20
[52] U.S. Cl. ................................... 435/198; 435/176; 435/179; 435/180; 435/188; 426/33
[58] Field of Search ............... 435/176, 198, 188, 179, 435/180; 426/33

[56] References Cited

U.S. PATENT DOCUMENTS

| | | | |
|---|---|---|---|
| 4,275,081 | 6/1981 | Coleman et al. | 435/176 |
| 4,472,503 | 9/1984 | Matsuo et al. | 435/176 |
| 4,719,178 | 1/1988 | Macrae et al. | 435/176 |
| 4,735,900 | 4/1988 | Urata et al. | 435/198 |

FOREIGN PATENT DOCUMENTS

| | | | |
|---|---|---|---|
| 140542 | 5/1985 | European Pat. Off. | 435/198 |
| 170431 | 2/1986 | European Pat. Off. | 426/33 |
| 6127087 | 10/1981 | Japan . | |
| 2168983 | 7/1986 | United Kingdom | 435/198 |

*Primary Examiner*—Robert A. Wax
*Assistant Examiner*—Mary E. Pratt
*Attorney, Agent, or Firm*—Wenderoth, Lind & Ponack

[57] ABSTRACT

A process for preparing an enzyme preparation useful for interesterification in the presence of little water. The process comprises drying a hydrated substance having lipase-activity while contacting the substance with a fatty acid derivative. The hydrated substance is an enzyme or enzyme preparation showing lipolytic activity in the presence of water sufficient to form an interface. The enzyme preparation is obtained by drying the hydrated substance while contacting the substance with fatty acid derivatives in an amount of 0.02 to 10% by weight. Suitable fatty acid derivatives include fatty acids, lower alcohol esters of fatty acids, surfactants and triglycerides.

3 Claims, No Drawings

PROCESS FOR PREPARING ENZYME PREPARATION

FIELD OF THE INENTION

The present invention relates to a process for preparing an enzyme preparation. More particularly, the enzyme preparation obtained by the process of the present invention shows excellent interesterification activity in the presence of very little water.

BACKGROUND OF THE INVENTION

The specificity of lipase for a substrate can be advantageously utilized for an interesterification reaction.

It is considerd that lipase essentially reacts at the interface between water and a lipid. Therefore, probably, because of the fact that the solubility of water in a fat or oil is about 0.2%, an interesterification reaction is often carried out in the presence of a certain amount of water to activate the enzyme, i.e. not less than 0.2% of water based on the substrate (see, for example, Japanese Patent Kokai No. 52-104506). However, in a reaction system containing such water, difficulties such as formation of a large amount of diglycerides are encountered.

The assignee company's Japanese Patent Kokai No. 56-127/087 discloses process for preparing an enzyme preparation having high interesterification activity even in the presence of much less water and, in the extreme case, even in a reaction system from which moisture of a substrate is removed as much as possible in an industrial scale.

OBJECTS OF THE INVENTION

The present inventors have found another process which can provide much higher interesterification activity.

The main object of the present invention is to provide a process for preparing an enzyme preparation which can show excellent interesterification activity in the presence of very little water.

This object as well as other objects and advantages of the present invention will become apparent to those skilled in the art from the following description.

SUMMARY OF THE INVENTION

According to the present invention, there is provided a process for preparing an enzyme preparation which comprises drying a hydrated substance having lipase-activity while contacting the substance with a fatty acid derivative.

Interesterification activity of the enzyme preparation obtained by the process of the present invention is remarkably improved, and the reaction time of interesterification as well as the amount of the enzyme to be used can be reduced.

DETAILED DESCRIPTION OF THE INVENTION

The term substance having "lipase-activity" herein means a lipolytic enzyme or a preparatin thereof ("a substance having lipase-activity" is herienafter referred to as an enzyme or an enzyme preparation unless otherwise stated). The enzyme preparation is not limited to a specific one and includes not only a so-called immobilized enzyme obtained by a conventional method such as sedimentation process, physical adsorption, ion adsorption, entrapping method, cross-linking method, covalent bonding method or the like, but also a endoenzyme and a microbial culture. Examples of a carrier for the enzyme preparation include diatomaceous earth, alumina, Celite, cellulose and other cellulose derivatives, porous glass, glass fiber, silicate gel, Florisil, ionexchanging resins, titanium dioxide, kaolinite, pearlite and the like, and the enzyme preparation may optionally contain other suitable additives such as di- or trihydric alcohol, polyhydroxy compounds, proteins and the like.

It is necessary that the enzyme or the enzyme preparation should exhibit "lipase-activity", i.e., lipolytic activity in the presence of water sufficient to form an interface. If the enzyme or the enzyme preparation does not have such an activity, it is impossible to give or enhance its interesterification activity. As the enzyme or the enzyme preparation, for example, an enzyme having specificity for $\alpha$- and $\beta'$- positions (e.g.., an enzyme derived from microorganisms of the genera Rhizopus, Aspergillus, and Mucor, pancreatic lipase, rice bran lipase and the like) is particularly useful, but an enzyme having no specificity for $\alpha$- and $\beta'$- positions (e.g.., an enzume derived from microorganisms of the genera Penicillium, Geotrichum, Corynebacterium, Candida and the like) can also be used.

In the process of the present invention, it is necessary to begin the drying step by using the enzyme or the enzyme preparation in a hydrated state, and said substance should be contacted with a fatty acid derivative at least at the beginning of the drying step.

The term "the hydrated state" means that an aqueous medium such as water, a buffer solution, aqueous acetone, aqueous alcohol or the like is uniformly diffused throughout the substance to be hydrated. It is preferred that the amount of the aqueous medium beyond the water retention capacity of the enzyme or the enzyme-containing substance (i.e., the amount of water which can be readily removed by a physical method) is as small as possible to shorten the time required for the drying step.

The fatty acid derivative which is contacted with the enzyme or enzyme preparation in the drying step includes, for example, fatty acids such as those having 2 to 22 carbon atoms, alkali metal salts of fatty acids, polycarboxylic acids (e.g., suberic acid, azelaic acid, etc.), substituted carboxylicacids (e.g., monochloro-oleic acid, etc.), hydroxy acid (e.g., ricinoleic acid, etc.), amino acid (e.g., glutamic acid, lysine, etc.), amide (e.g., lauryl amide, oleil amide, etc.), and fatty acid ester such as lower alcohol esters of fatty acid (e.g., ethyl oleate, ethyl laurate, etc.), higher alcohol esters of fatty acids (e.g., docosenyl eicosanoate, lauryl laurate, etc.), sorbitan fatty acid ester (e.g., sorbitan monoleate, sorbitan mono lurate, etc.), lecithin, other surfactants (e.g., glycerol mono oleate, propylene glycol mono oleate, sucrose fatty acid ester, etc.) and triglycerides (e.g., triolein, trilaurin and other animal and vegetable oils such as soybean oil, rapeseed oil, safflower oil, sunflower oil, palm oil, etc.) and the like.

Although the mechanism for enhancing interesterification activity in the process of the present invention is unclear, it is considered that the fatty acid derivative advantageously affects a certain portion of the enzyme during its contact with the enzyme or the enzyme preparation and contributes to maintain the configuration of the enzyme or the enzyme preparation suitable for interesterification during the drying step.

The time and method for addition of the fatty acid derivative is not particularly limited except that the derivative should contact with the enzyme or enzyme preparation during drying. Preferably, the derivative can be used by dissolving or emulsifying it in an aqueous solution of the enzyme in which the enzyme is mixed with a carrier, or by spraying it on the hydrated enzyme or enzyme preparation, thereby a relatively small amount of fatty acid derivative can be uniformly dispersed effectively.

In order to employ the dispersion method as described above, in general, it is desirable that the fatty acid derivative be water-soluble or be in liquid form at room temperature. Further, depending upon a praticular use of the enzyme preparation obtained by the present invention, it is desirable to select an appropriate fatty acid derivative to avoid contamination of an enzyme substrate. According to the present inventors' study, an ester of a saturated fatty acid having not more than 12 carbon atoms or an unsaturated fatty acid having not more than 22 carbon atoms with a monohydric lower alcohol such as ethyl laurate, ethyl oleate or the like is most suitable.

The amount of the fatty acid derivative to be used in the present invention is usually not less than 0.02% by weight based on the weight of the enzyme on the enzyme preparation (calculated as a total amount of solids including a carrier) to be used, otherwise enhancement of interesterification activity is not expected. However, when the amount is more than 10% by weight based on the weight of the enzyme on the enzyme preparation, further increase in activation of interesterification activity is scarcely expected.

In the drying step, generally, it is of importance to keep a drying rate slow at the beginning, i.e., until the moisture of the hydrated substance will decrease to some extent. The drying rate varies according to a particular substance to be used which contains the enzyme, a particular type of a carrier and the like. Therefore, it can not be defined uniformly. However, it can be experimentally determined with ease as follows. That is, firstly, the entire drying step is carried out at several different drying rates to find out a suitable drying rate. Then, the time when the drying rate can be made faster is determined. Of course, drying can also be carried out at a constant slow drying rate over the entire drying step without any severe problem in productivity. The initial drying rate, in general, is desirably not higher than 0.5 expressed as decrease in water content per hour (i.e., the decrease in the ratio of the material to the dried (kg) to the dry weight of the material (kg) per hour). When powder or granules having particle size of about 2 mm and having high water retention characteristics are used, the rate of not higher than 0.3 to 0.25 (decrease in water content per hour), respectively, is more desirable. In view of the quality of the enzyme product obtained by the process of the present invention, the most preferred rate is in the range of not higher than 0.1 expressed as decrease in water content.

The means for drying includes drying under reduced pressure as well as a method by contacting with gas (e.g.., air, nitrogen and other inert gases) having relatively lower humidity such as ventilating drying, blast drying, permeation drying, hot-air drying, a method by contacting with fluid (liquid having certain compatibility with water without denaturating protein such as glycerin, propylene glycol, and the like) having relatively lower humidity, or a combination thereof. The means for controlling the drying rate includes control of a saturation deficit with the fluid used for drying (i.e., control of moisture contained in the fluid), control of heat energy to be given to the drying fluid or the substance to be dried, and the like. However, excessive heat supply at drying which results in inactivation of the enzyme should be avoided. At the beginning of the drying, the preferred temperature of the medium is generally not more than 50° C., and the preferred temperature of the enzyme or the enzyme preparation is generally not more than 20° C.

Although the extent of drying varies depending on a particular use of the enzyme product obtained by the process of the present invention, generally, it is desired that the water content of the product becomes not more than about 10% by weight. Particularly, when the product is used in a system having low moisture, the product is desirably dried to have lower water content, for example, not more than 5% by weight. The dehydration of the enzyme preparation which has been dried to some extent can also be carried out by, for example, immersing the preparation itself in a substrate such as glycerides to consume water therein for hydrolyzation of the substrate.

The following Examples further illustrate the present invention in detail but are not to be construed to limit the scope thereof. In the Examples, all "parts" and "%'s" are by weight unless otherwise stated.

EXAMPLE 1

One part of commercially available lipase (derived from *Rhizopus delemar*) was dispersed in 3.5 parts of chilled water and further 2.5 parts of kaolinite was dispersed in this dispersion to hydrate a mixture of lipase and kaolinite. Then, 0.0005–0.5 part of ethyl oleate was sprayed with mixing. The mixture was dried at 20° C. under reduced pressure to give an enzyme preparation having a water content of 2.5 %.

| Ethyl oleate (parts) (% based on the dried enzyme) | | Interesterification activity* |
|---|---|---|
| A | 0 (0.000%) | 12.4 |
| B | 0.0005 (0.014%) | 13.2 |
| C | 0.005 (0.14%) | 27.5 |
| D | 0.05 (1.4%) | 37.8 |
| E | 0.5 (14%) | 36.3 |

*Data were obtained according to the method for measuring Ka value described in Japanese Patent Laid Open Publication No. 51-35449. 35449.

Various amounts of the enzyme prepration A or D were reacted with 100 parts of substrate obtained by mixing palm mid fraction and ehtyl stearate (1 : 1) (moisture of the substrate: 0.1%) at 40 C. (water content of the system: 0.08 %). The time (days) required to obtain about 80% of interesterification reaction rate was as follows.

| Enzyme preparation | Days required for 80% reaction rate Amount used | | |
|---|---|---|---|
| | 2 parts | 3 parts | 5 parts |
| A | 8 | 5 | 3 |
| D | 3 | 2 | 1 |

Further, interesterification reaction was carried out by using 2 parts of the enzyme preparation in a system to which water was added in such an amount that water content of the system was 0.5%. The time required to obtain about 80% interesterification reaction rate was 4 days for the preparation A, while 2 days for the preparation D. Therefore, good interesterification activity was shown even in a system containing relatively a large amount of water. However, the amount of diglycerides formed was not more than 5% in the former system containing 0.08% of water, while it was about 18% in the latter system containing 0.5% of water.

EXAMPLE 2

0.5 to 2.0 parts of commercially available lipase (derived from *Rhizopus nibeus*) and 0.05 part of ethyl laurate were dispersed in 3.0 parts of chilled water and 2.5 parts of diatomaceous earth was further dispersed in said dispersion to obtain a hydrated substance. The substance was packed in a column and air of 50% humidity was passed through the column to obtain an enzyme preparation having water content of 1.8%.

The interesterification activity (Ka value as described above) and the corresponding amount of the enzyme used for the resulting enzyme preparation (amount of commercially available lipase without containing the carrier) are shown in the following table.

| Amount of Enzyme used (parts) | | 0.5 | 1.25 | 2.0 |
|---|---|---|---|---|
| Ka value | With laurate | 28.3 | 53.7 | 79.1 |
| | Without laurate | 22.5 | 42.4 | 54.6 |

Also, ethyl stearate was used instead of ethyl laurate. However, dispersion in the enzyme solution was somewhat inferior.

EXAMPLE 3

In the same manner as described in Example 1, an exzyme preparation was obtained except that oleic acid, sorbitan mono-oleate, sodium laurate, glycerol mono-oleate, triolein or sucrose fatty acid ester having HLB of about 5 was used instead of ethyl oleate (0.05 parts). The Ka value of interesterification activity was 32.1, 35.3, 39.2, 33.4, 31.6 or 33.8, respectively.

What is claimed is:

1. A process for preparing an enzyme preparation which comprises drying a hydrated substance having lipase-activity while contacting the hydrated substance with a fatty acid derivative selected from the group consisting of fatty acids, lower alcohol esters of fatty acids, surfactants and triglycerides, the amount of said fatty acid derivative being 0.02 to 10% by weight based on the weight of said hydrated substance calculated as a total amount of the solids contained therein.

2. A process according to claim 1, wherein the substance having lipase-activity is a lipolytic enzyme or a lipolytic enzyme preparation.

3. A process according to a claim 1, wherein the fatty acid derivative is in liquid form at room temperature.

* * * * *